United States Patent [19]

Rosenbaum et al.

[11] Patent Number: 5,066,377
[45] Date of Patent: Nov. 19, 1991

[54] METHOD AND DEVICE FOR PRODUCING A CONTROLLABLE AND REPRODUCIBLE TEMPERATURE GRADIENT AND USE THEREOF

[75] Inventors: Volker Rosenbaum, Meerbusch; Detlev Riesner, Düsseldorf, both of Fed. Rep. of Germany

[73] Assignee: Diagen Institute für molekularbiologische Diagnostik GmbH, Düsseldorf, Fed. Rep. of Germany

[21] Appl. No.: 545,111

[22] Filed: Jun. 29, 1990

Related U.S. Application Data

[63] Continuation of Ser. No. 317,058, Feb. 28, 1989, abandoned, which is a continuation of Ser. No. 67,882, Jun. 30, 1987, abandoned.

[30] Foreign Application Priority Data

Jul. 4, 1986 [DE] Fed. Rep. of Germany ....... 3622591

[51] Int. Cl.[5] .................. G01N 27/26; B01D 57/02
[52] U.S. Cl. ......................... 204/182.8; 204/299 R; 204/182.7
[58] Field of Search ............. 204/299 R, 182.8, 180.1, 204/182.7, 182.9

[56] References Cited

U.S. PATENT DOCUMENTS

| | | |
|---|---|---|
| 2,888,392 | 5/1959 | Grassman et al. |
| 3,402,118 | 9/1968 | Mutter ........................... 204/299 R |
| 3,801,467 | 4/1974 | Nobe et al. ..................... 374/15 X |
| 4,679,615 | 7/1987 | Livne ............................ 165/58 X |

OTHER PUBLICATIONS

Thatcher et al., "Denaturation of Proteins and Nucleic Acids by Thermal-Gradient Electrophoresis", Biochem. J. (1981), 197, pp. 105-109.

Blasius et al., "High-Voltage Paper Ionophoresis in Temperature Gradients and Non-Aqueous Solvents," J. Chromatgr., 108 (1975), 1, pp. 323-328.

Blasius et al., "Apparatus for High-Voltage Ionophoresis in Temperature Gradients", J. Chromatgr., 135 (1977), 2, pp. 53-60.

Giddings, "Field Flow Fractionation", Analytical Chemistry, vol. 53, No. 11, pp. 1170-1178 (1981).

*Primary Examiner*—John Niebling
*Assistant Examiner*—John S. Starsiak, Jr.
*Attorney, Agent, or Firm*—Wegner, Cantor, Mueller & Player

[57] ABSTRACT

A method and a device for producing a controllable and reproducible temperature gradient in a predetermined direction of heat-conducting plates for the separation of mixtures of substances in sheet-shaped separating media wherein one edge of a plate is heated by means of one or more controllable heating means and the opposite edge of the plate is cooled by one or more controllable cooling means. In this way, the energy flows through the heating means and of the cooling means are greater than the energy flow across the plate. The method and device are suitable for separating mixtures of substances wherein at least one component undergoes a thermal conversion within the temperature range of the temperature gradient. Therefore, they are suitable for the detection of and differentiation between viroids, satellite RNAs, viruses containing double-strand or circular nucleic as well as for the analysis of protein-nucleic acid complexes and for the analysis of mutations.

19 Claims, 4 Drawing Sheets

5,066,377

METHOD AND DEVICE FOR PRODUCING A CONTROLLABLE AND REPRODUCIBLE TEMPERATURE GRADIENT AND USE THEREOF

This application is a continuation of U.S. application Ser. No. 07/317,058 filed Feb. 28, 1989, which is a continuation of U.S. application Ser. No. 07/067,882 filed June 30, 1987, both now abandoned.

BACKGROUND OF THE INVENTION

The present invention relates to a method for producing a controllable and reproducible temperature in a pre-determined direction of heat-conducting plates for the separation of mixtures of substances in sheet-shaped separating media. Furthermore, the invention relates to a device for producing such a temperature gradient and to its use for the separation of substance mixtures, wherein at least one component undergoes a thermal conversion within the temperature range of temperature gradient.

It has been known that a number to naturally occurring substances having higher molecular weights undergo conversions or irreversible changes at increasing temperatures and that these changes may be analytically evaluated. D. R. Thatcher and B. Hodson, in Biochem. (1981) 197, pp. 105-109, investigated the denaturation of proteins and nucleic acids by means of the application of a thermal gradient during electrophoresis and observed that thermally caused changes can be rendered visible thereby. For producing a temperature gradient they designed an apparatus which could be positioned on both sides of a vertical polyacrylamide gel plate, whereupon thermostatically controlled water at different temperatures is passed through both ends of the aluminum plates. The two plates were connected to each other in series and it was assumed that an identical thermal gradient thereby was formed. However, there are disadvantages to this device, in that it is not only complicated in design and difficult to handle, but also suffers from a basic error since a controllable and reproducible temperature gradient cannot be established. An undesired and interfering temperature gradient was formed between the inlet and outlet of the water bath by the flow through the two plates connected in series. This in turn leads to an occurrence of different temperatures and non-parallel temperature gradients in the two plates. This results in the gel electrophoresis plate having different temperatures at its front and back surfaces.

SUMMARY OF THE INVENTION

First, it is an object of the present invention to produce a controllable and reproducible temperature gradient in a pre-determined desired direction of heat-conducting plates for the separation of mixtures of substances in sheet-shaped separating media. This object is intended to be attained with as low an expense as possible with respect to design and construction of an apparatus, while nevertheless ensureings that minimum malfunctions occur.

This object is attained in a surprisingly simple manner by providing a device comprising only one plate and by having one edge of the plate heated by means of one or more heating means and having the opposite edge of the plate cooled by one or more controllable cooling means.

The rate at which energy is supplied by the heating means and the cooling means is greater than the rate at which energy flows across the plate. Furthermore, the rate at which energy flows across the plate is greater than the rate at which energy flows normal to the plate through the sheet-shaped separating medium.

DETAILED DESCRIPTION OF THE INVENTION

Investigations of rectangular plates having one edge heated by a heating means and having the opposite edge of the plate cooled by a cooling means showed that in this manner a virtually linear temperature gradient can be generated in the plate and that this temperature gradient is transferred from the plate to the contiguous sheet-shaped separating media. Furthermore, it has been shown that if the sheet-shaped separating medium is covered with a heat-insulating means at the surface away from the plate, the same temperature gradient is formed throughout the whole layer. Thus, the temperatures on both surfaces of the separating medium are approximately identical. Therefore, malfunctions and interferences due to different degrees of heating caused by one plate on each side of the separating medium cannot occur.

Figure 1:
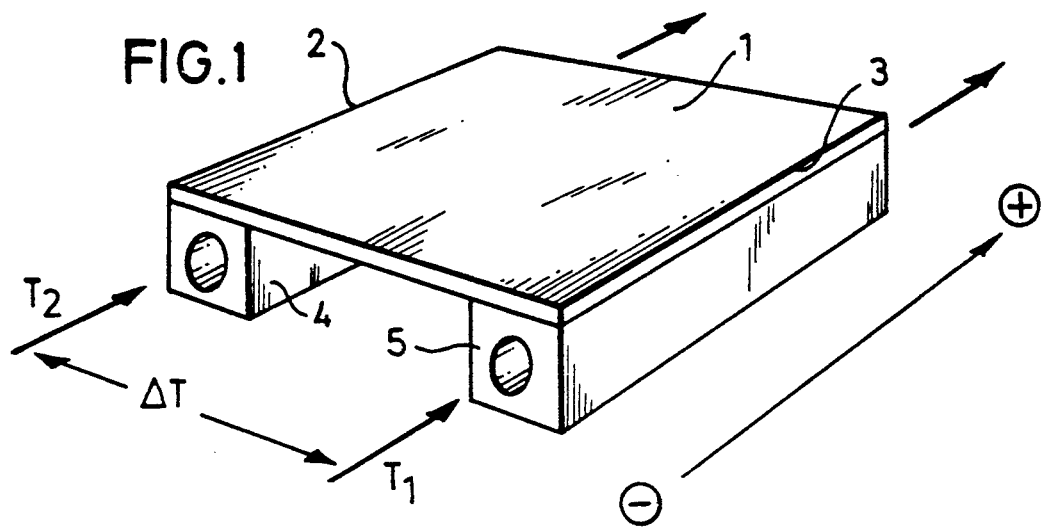
FIG. 1 is a perspective view of a first preferred embodiment of the present invention.

In one preferred embodiment, shown in FIG. 1; the heating of one edge of the plate and the cooling of the opposite edge of the plate can be effected by means of thermostatically controlled liquid baths. Alternatively, heating of the one edge may be effected by electric heating such as by heating wires or by Peltier elements.

In order to ensure that, upon use of thermostatized liquid baths, the energy flow of the heating means and of the cooling means is greater than the energy flow through the plate, it is not entirely sufficient to provide bores at the plate ends through which the bath liquid may flow. Metal blocks having relatively large dimensions are preferably provided, the blocks having holes therethrough and disposed over a large area of the edges of the plate. Preferably, metal blocks containing a single bore or double bores are employed which have an external edge distinctly wider than the thickness of the heat-conducting plate.

In the case of metal blocks comprising one bore, due to the energy flow therethrough, the plate forms some temperature gradient between inlet and outlet. This temperature gradient is then passed to the plate as a relatively minor error in temperature gradient when taken over the entire plate. In order to avoid even these adverse effects on the temperature gradient in the plate, metal blocks with two bores are preferably used, through which the respective liquid bath is subsequently pumped in both directions. Thereby, the temperature gradient between the entering and exiting bath liquid becomes smaller and will be compensated for within the metal block. It will also be possible to compensate somewhat for this error by selecting, in blocks comprising a single bore, an angle deviation from the parallel arrangement which corresponds to the temperature gradient and, thus, balances the smaller temperature difference between the outflows by a reduced distance which then will result in the same gradient. Substantially more troublesome than a non-ideal gradient are the temperature deviations on the upper and lower surfaces of sheet-shaped separating media upon the use of two plates, the, temperature gradients of which are not fully coincident, as has the case in the state of prior art.

A further advantage of the process according to the present invention is that it is possible to produce not only a temperature gradient in a direction vertical to the pass line, but also a temperature gradient in the direction parallel to the pass line. Thus, it is possible to investigate purified fractions chromatographicaly uniform in appearance.

In some cases, it has been determined that the substance mixtures are susceptible to another separation under the action of a parallel temperature gradient. This is due to the fact that individual components of the mixture while uniform in appearance, exhibit different thermal behavior and, hence, upon migrating through the sheet-shaped separating medium, undergo conversion at different locations and, thus, change their migration velocity. If a parallel temperature gradient is used, it is further possible to investigate several samples at the same time.

If the process according to the invention is employed using gel plates for electrophoresis, then, for example, it is possible to detect and to differentiate viroids, satellite ribonucleic acids to viruses and viruses comprising double-strand RNA. Furthermore, it is possible to analyze protein-nucleic acid complexes as well as mutations, as these are also thermally distinguishable in a very specific manner. Previously, some of these separations could only be solved by means of the gradient plates for gel electrophoresis, which plates are very difficult to reproduce and extremely difficult to prepare. More particularly, such gradient plates having an urea gradient or a gradient of an inhibitor have become known (of. L. S. Lerman et.al., Ann. Rev. Biophys. Bioeng., 1984, 13, pp. 399–423).

A particularly simple and preferred embodiment of the device according to the invention is shown in FIG. 1, the dimensions of which device are suitable to use in connection with a commercially available gel electrophoresis apparatus, i.e. the LKB 2117 Multiphor II.

Figure 3:
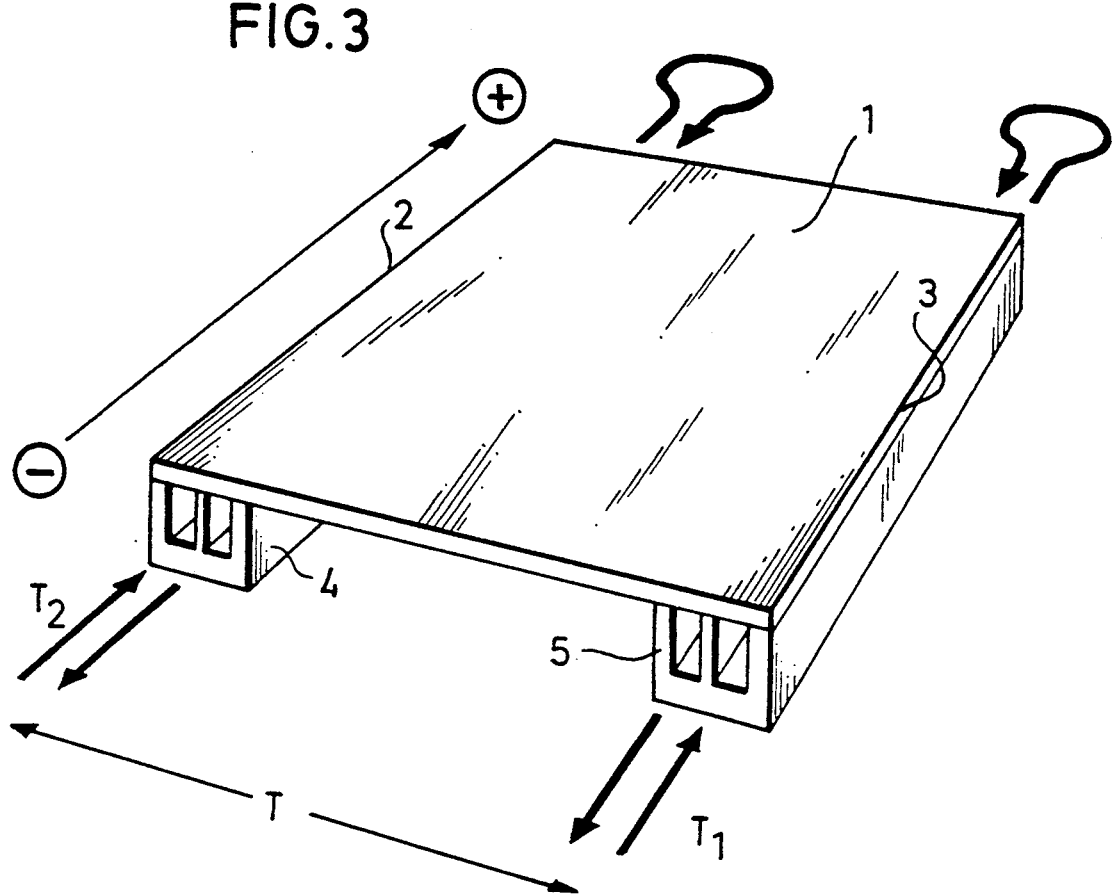
FIG. 3 is a perspective view of a second preferred embodiment of the present invention.

FIGS. 1 and 3 both shown a heat conducting plate having a controllable heating device 4 attached along one edge 2 and a controllable cooling device 5 attached along an opposing edge 3. In the embodiment of FIG. 1, the heating device 4 and cooling device 5 each include a metal block having a single bore through which water at temperature $T_2$ and $T_1$, respectively, can be flowed. In the embodiment of FIG. 3, the heating and cooling devices have double-bore metal blocks through which the water travels in opposite directions.

Figure 2:
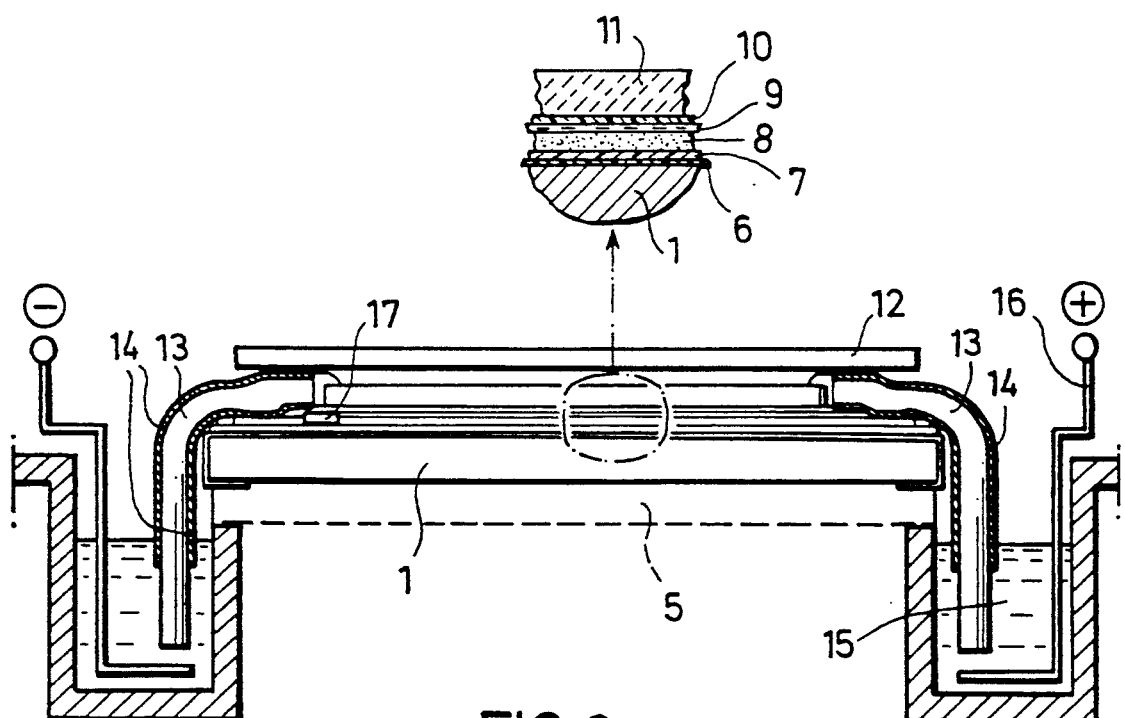
FIG. 2 is a side elevational view of the present invention used in a temperature gradient gel electrophoresis apparatus.

FIG. 2 shown the device of the present invention employed in an apparatus for temperature gradient gel electrophoresis. As seen in that figure, a layer of gel 8 is located on the cooper plate 1. The cooling device 5 can be seen attached to the plate, whereas the heating plate 4 is located behind the cooling plate, as viewed in FIG. 2. A layer of polytetrafluoroethylene (PTFE) 6 and a film 7 are disposed between the gel and the plate. The PTFE provides electrical insulation, while the film supports the gel. A liquid film 9 is placed on top of the gel, and a cover film 10 is placed over the liquid film 9. A glass plate 11 is positioned over the cover film 10. Electrode contact cloths 13 having a polyethylene film 14 thereon extend between the glass plate 11 and electrode buffer basins 15. Positive and negative electrodes 16 are placed in the buffer basins 15. A gel pouch 17 is provided adjacent the layer of gel 8.

Figure 4:
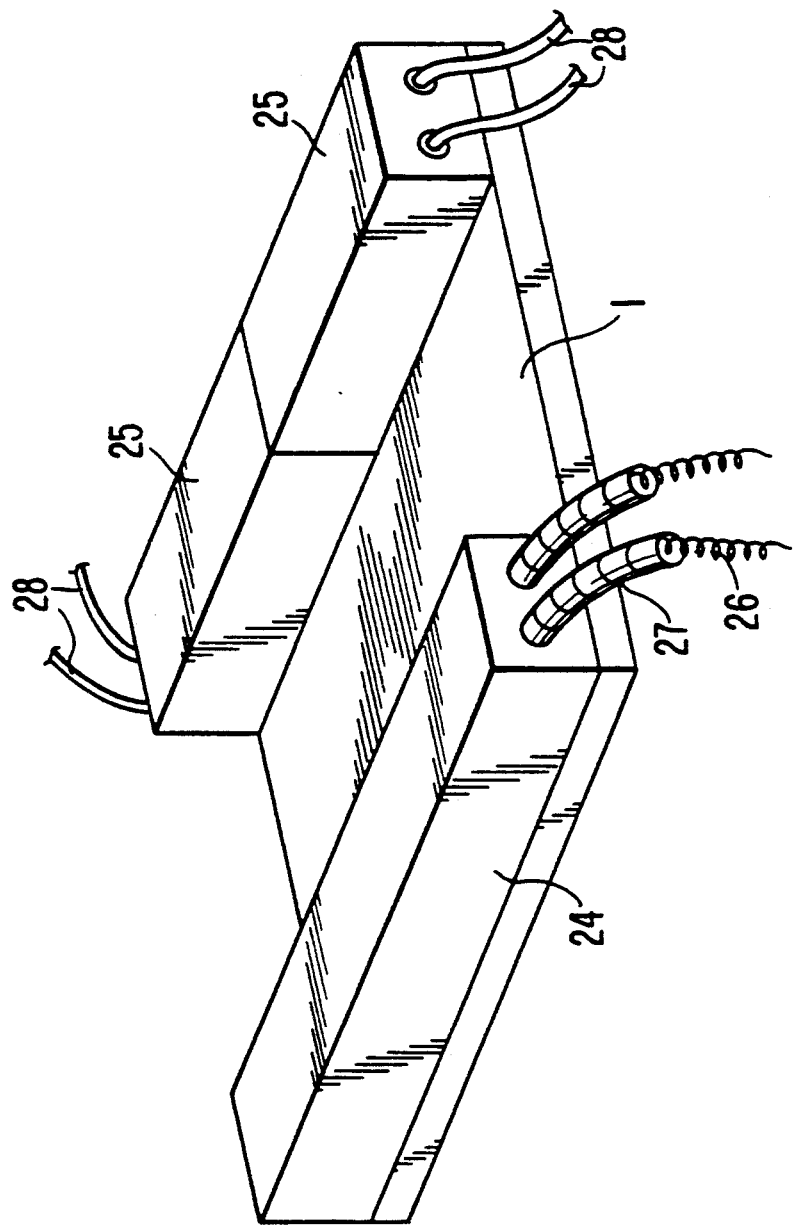
FIG. 4 is a perspective view of a third preferred embodiment of the invention.

FIG. 4 shown an alternate embodiment of the device of the present invention wherein the heat-conducting plate 1 is connected to an electric heater 24 and a pair of Peltier elements 25. The electric heater is connected to a power source via wires 26 having electrical insulation 27, and the Peltier elements are connected to a power source via wires 28.

Figure 5:
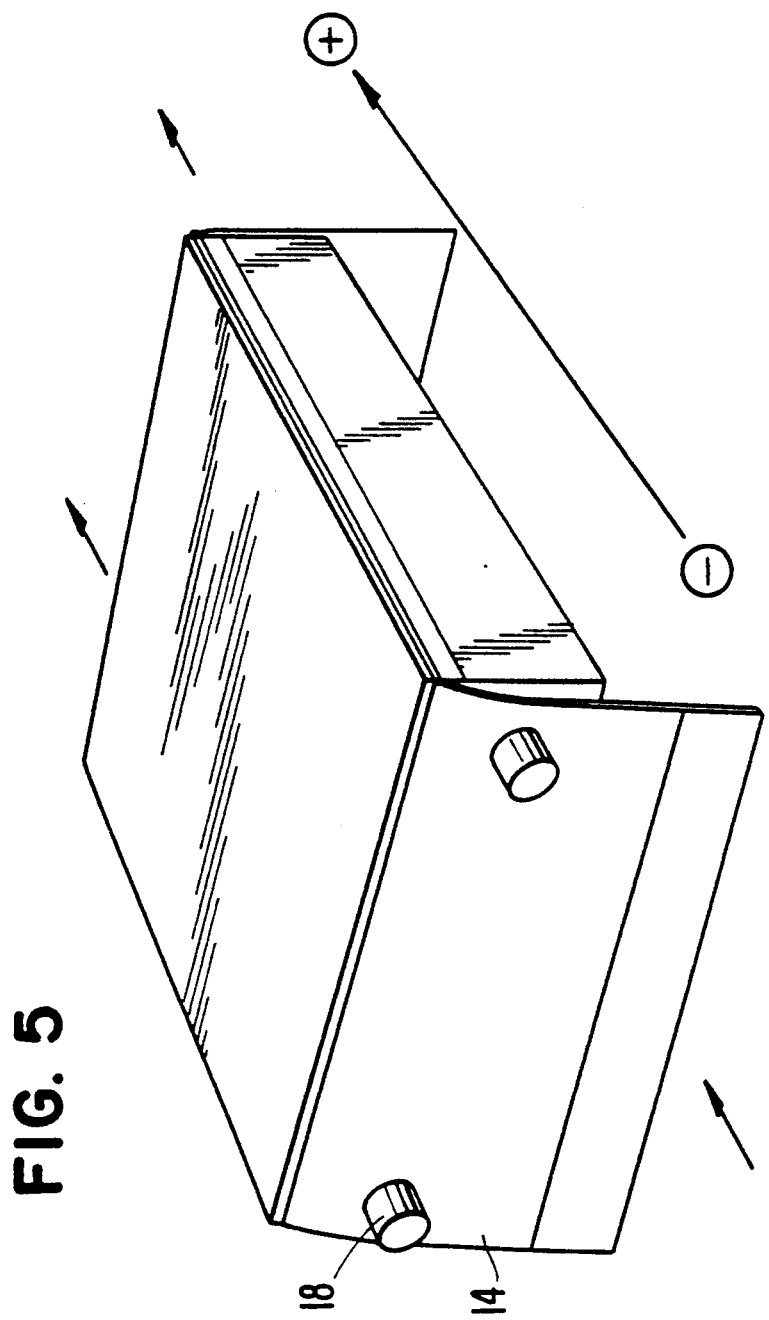
FIG. 5 is a view of the embodiment of FIG. 1 further including features of the apparatus of FIG. 2.

FIG. 5 shown the embodiment of FIG. 1, further including polyethylene film 14 which has been perforated by brass connectors 18.

In order to carry out the temperature gradient gel electrophoresis, the gel is preferably applied in a horizontal position on the thermostatizing plate according to FIG. 1. The electric field is produced in the gel via two filter papers or sponge cloths connected to buffer-filled electrode chambers. In place of the filter papers commercially available for horizontal electrophoreses, household sponge cloths boiled in distilled water have proven to be useful, since they have a higher absorption capacity and after autoclaving show less microbiological contaminations.

The thermostatizing plate consists, for example, of two cuboid copper columns of square cross sections (210 nm × 30 mm × 30 mm) and one central cylindrical bore 15 mm in diameter. They are soldered to the opposite sides of one surface of a copper plate of 210 mm × 190 mm × 5 mm. The ends of the cylindrical bores are furnished with brass hose connectors 18 to which the inlet and outlet tubings of two water thermostats are connected. The lower limit of the temperature gradient ($T_1$) is defined by a coolable Julabo F20-HC thermostat, and the upper limit ($T_2$) is defined by a Haake F3 thermostat. After the thermostats have been connected to the thermostatizing plates, within a few minutes a constant temperature gradient is observed. The temperature gradient between inlet and outlet of the copper blocks was less than 0.5° C. The maximum temperature gradient provided by the apparatus was 70° C. of the temperature above and below the gel resulted in maximum deviations of 1° C. Electrophoresis was first started at $T_1 = T_2 = 10°$ C. and a voltage of 100 V, and was stopped again when it could be estimated that the sample subjected to the investigation had fully permeated into the gel matrix. Then the voltage was disconnected, the gel including the charging pouch was overlaid with a layer of electrode buffer, and was covered without leaving air bubbles within the hydrophilic surface of a gel bond film. Measuring and wrapping the sponge cloths leading into the buffer-filled electrode vessels with a commercially available household film has proven to provide effective protection for exsiccation. For the purpose of thermal insulation, two glass plates each 5 mm in thickness are placed on the cover film, which glass plates allow the motion of the colorant indicators in the gel to be monitored. Then the temperature gradient is produced by adjusting the heating and cooling. It takes less than 5 minutes to form a linear temperature gradient on the thermostatizing plate and in the gel. In order to ensure that the quilibrium state of the confirmation of the samples under investigation is reached, equilibrating was providently continued for another 10 minutes. This period of equilibrating time is a compromise between the goal of the maximum possible equilibration of the sample being investigates and the goal of the minimum possible diffusion of the sample into the gel matrix. Thereafter, voltage of 300 V is turned on. The voltage is switched off, once it is determined from the indicator that the sample has nearly arrived at the other end of the gel plate.

In the meantime the method has been successfully practiced for the detection of and differentiation between viroids, the diagnosis of viruses containing double-strand or circular nucleic acid, and for the detection and characterization of various strains of, for example, rotavirus.

Furthermore, it was possible to furnish experimental evidence of the symptom-regulating RNAs by way of the examples of cucumber mosaic virus and peanut stunt virus, and unambiguously to distinguish between symptom-enhancing and symptom-weakening satellite RNAs. Finally, an analysis of protein-nucleic acid complexes has been successfully carried out, and experimental evidence has been furnished, of that by one mutation in a regulatory sequence, a malfunction readily to be analyzed was determinable. Thus, this method is also suitable for analyzing mutations in proteins. Using the example of the potato spindle tuber viroid, different strains distinguished from one another by only 1 of 359 bases and leading to disease symptoms different in intensities could be separated and quantitatively analyzed. Such an analysis will not be restricted to viroids, but generally can be employed for analyzing mutations, and even point mutations in nucleic acids.

We claim:

1. An electrophoresis device, comprising:
   a sheet-shaped separating medium;
   a means for producing a linear controllable and reproducible temperature gradient in said sheet-shaped medium, comprising a single heat conducting plate, said heat conducting plate opposed to a first surface of said sheet-shaped separating medium, controllable heating means for heating one edge of said plate, and controllable cooling means for cooling an opposing edge of said plate, said heating means comprising a first block connected to the one edge of the plate and having a bore therethrough, said cooling means comprising a second block attached to the opposing edge of the plate and having a bore therethrough;
   an insulation means opposed to a surface of said sheet-shaped separating medium opposite said first surface for thermally insulating said sheet-shaped separating medium such that a uniform temperature can be maintained through the separating medium; and
   a means for producing an electrical field in said sheet-shaped separating medium to create a potential gradient across said sheet-shaped separating medium.

2. The electrophoresis device as claimed in claim 1, wherein said sheet-shaped separating medium is a layer of gel disposed over said heat conducting plate, and further comprising an electric insulating film and a film for supporting the gel interposed between the layer of gel and the heat conducting plate.

3. The apparatus of claim 1, wherein the temperature gradient direction in said sheet-shaped separating medium is perpendicular to the potential gradient direction is said sheet-shaped separating medium.

4. An electrophoresis device, comprising:
   a sheet-shaped separating medium;
   a means for producing a controllable and reproducible temperature gradient in said sheet-shaped medium, comprising a heat conducting plate, controllable heating means for heating one edge of said plate, and controllable cooling means for cooling an opposing edge of said plate, said heating means comprising a first block connected to the one edge of the plate and having a bore therethrough, said cooling means comprising a second block attached to the opposing edge of the plate and having a bore therethrough, wherein said first and second blocks have substantially greater thickness than does said heat conducting plate; and
   a means for producing and electrical field in said sheet-shaped separating medium to create a potential gradient across said sheet-shaped separating medium.

5. The electrophoresis device as claimed in claim 4, wherein said heating means further comprises a first thermostatically controlled liquid bath and means for supplying liquid from said first bath to the bore through said first block, and said cooling means further comprises a second thermostatically controlled liquid bath and means for supplying liquid from said second bath to the bore through said second metal block.

6. The apparatus of claim 5, wherein the temperature gradient direction in said sheet-shaped separating medium is perpendicular to the potential gradient direction in said sheet-shaped separating medium.

7. The electrophoresis device as claimed in claim 5, wherein the first block and the second block each have two bores therethrough, and the liquid from the first bath flows in opposing directions through the bores of the first block, and the liquid from the second bath flows in opposing directions through the bores of the second block.

8. An electrophoresis device, comprising:
   a sheet-shaped separating medium comprising a layer of gel;
   a means for producing a linear controllable and reproducible temperature gradient in said sheet-shaped medium, comprising a single heat conducting plate, said heat conducting plate opposed to a first surface of said sheet-shaped separating medium, controllable heating means for heating one edge of said plate, and controllable cooling means for cooling an opposing edge of said plate, said heating means comprising at least one electric heater or Peltier element disposed along the one edge of the plate and operating at a first temperature, and said cooling means comprising at least one Peltier element disposed along the opposing edge of the plate and operating at a second temperature;
   an insulation means opposed to a surface of said sheet-shaped separating medium opposite said first surface for thermally insulating said sheet-shaped separating medium such that a uniform temperature can be maintained through the separating medium; and
   a means for producing an electrical field in said sheet-shaped separating medium to create a potential gradient across said sheet-shaped separating medium.

9. The electrophoresis device as claimed in claim 8, further comprising a film of polytetrafluoroethylene and a film for supporting the gel interposed between the layer of gel and the heat conducting plate.

10. The apparatus of claim 8, wherein the temperature gradient direction in said sheet-shaped separating medium is perpendicular to the potential gradient direction in said sheet-shaped separating medium.

11. A method for separating a mixture of substances in a sheet-shaped separating medium, comprising:
placing a single heat-conducting plate in thermal connection with the sheet-shaped separating medium at a first surface of said sheet-shaped separating medium and placing insulation means for thermally insulating said sheet-shaped separating medium such that a uniform temperature can be maintained through the sheet-shaped separating medium at a surface of said sheet-shaped separating medium opposite to said first surface;
creating a linear controllable and reproducible temperature gradient across the heat-conducting plate, comprising attaching a first block having a bore therethrough to one edge of the heat conducting plate, connecting a second block having a bore therethrough to an opposing edge of the heat conducting plate, supplying liquid at a first predetermined temperature through the bore of the first block so as to controllably heat said one edge, and supplying liquid t a second predetermined temperature through the bore of the second block so as to controllably cool said opposing edge;
applying an electrical field to said sheet-shaped separating medium to create a potential gradient across said sheet-shaped separating medium; and
causing one substance in the mixture to undergo a thermal conversion within the controllable and reproducible temperature gradient, thereby separating said substances.

12. The method as claimed in claim 11, wherein said sheet-shaped separating medium is a layer of gel disposed over said heat conducting plate, and further comprising interposing an electric insulation film and a film for supporting the gel between the layer of gel and the heat conducting plate.

13. The method of claim 11, wherein the temperature gradient direction in said sheet-shaped separating medium is perpendicular to the potential gradient direction in said sheet-shaped separating medium.

14. A method for separating a mixture of substances in a sheet-shaped separating medium, comprising:
placing a heat-conducting plate in thermal connection with the sheet-shaped separating medium;
creating a controllable and reproducible temperature gradient across the heat-conducting plate, comprising attaching a first block having a bore therethrough to one edge of the heat conducting plate, connecting a second block having a bore therethrough to an opposing edge of the heat conducting plate, supplying liquid at a first predetermined temperature through the bore of the first block so as to controllably heat said one edge, and supplying liquid at a second predetermined temperature through the bore of the second block so as to controllably cool said opposing edge;
applying an electrical field to said sheet-shaped separating medium to create a potential gradient across said sheet-shaped separating medium; and
causing one substance in the mixture to undergo a thermal conversion within the controllable and reproducible temperature gradient, thereby separating said substances,
wherein the first block attached to said one edge and the second block attached to said opposing edge have substantially greater thickness than does said heat conducting plate.

15. The method as claimed in claim 14, wherein the first block and the second block each have two bores therethrough, wherein the step of supplying liquid at a first predetermined temperature comprises supplying said liquid at the first predetermined temperature in opposing directions through the bores of the first block, and wherein the step of supplying liquid at a second predetermined temperature comprises supplying said liquid at the second predetermined temperature in opposing directions through the bores of the second block.

16. The method of claim 14, wherein the temperature gradient direction in said sheet-shaped separating medium is perpendicular to the potential gradient direction in said sheet-shaped separating medium.

17. A method for separating a mixture of substances in a sheet-shaped separating medium comprising a layer of gel, comprising:
placing a single heat-conducting plate in thermal connection with the sheet-shaped separating medium at a first surface of said sheet-shaped separating medium and placing insulation means for thermally insulating said sheet-shaped separating medium such that a uniform temperature can be maintained through the sheet-shaped separating medium at a surface of said sheet-shaped separating medium opposite to said first surface;
creating a linear controllable and reproducible temperature gradient across the heat-conducting plate, comprising connecting at least one electric heater or Peltier element operating at a first pre-determined temperature to one edge of the heat conducting plate, and connecting at least one Peltier element operating at a second predetermined temperature to an opposing edge of the heat conducting plate;
applying an electrical field to said sheet-shaped separating medium to create a potential gradient across said sheet-shaped separating medium; and
causing one substance in the mixture to undergo a thermal conversion within the controllable and reproducible temperature gradient, thereby separating said substances.

18. The method as claimed in claim 17, further comprising interposing a film of polytetrafluoroethylene and a film for supporting the gel between the layer of gel and the heat conducting plate.

19. The method of claim 17, wherein the temperature gradient direction in said sheet-shaped separating medium is perpendicular to the potential gradient direction in said sheet-shaped separating medium.

* * * * *